United States Patent [19]

Thomas

[11] Patent Number: 4,541,269
[45] Date of Patent: Sep. 17, 1985

[54] GAS CHROMATOGRAPH DETECTOR

[75] Inventor: Larry C. Thomas, Corvallis, Oreg.

[73] Assignee: The State of Oregon acting by and through State Board of Higher Education for and on behalf of Oregon State University, Eugene, Oreg.

[21] Appl. No.: 517,662

[22] Filed: Jul. 27, 1983

[51] Int. Cl.[4] .............................................. G01N 31/08
[52] U.S. Cl. ...................................... 73/23.1; 250/343
[58] Field of Search .................. 73/23.1, 23; 250/343, 250/373

[56] References Cited

U.S. PATENT DOCUMENTS 3,920,334 11/1975 Steichen et al. ................ 250/343
4,411,867 10/1983 Ostrander ......................... 250/373
4,469,946 9/1984 Tanaka et al. ................... 250/343

Primary Examiner—Stephen A. Kreitman
Attorney, Agent, or Firm—Kolisch, Hartwell & Dickinson

[57] ABSTRACT

A gas chromatographic detector for detection of compounds which fluoresce as a photo-response to light. The detector utilizes a remotely located light source for fluorescent excitation of a compound in a gas phase, and includes apparatus for the measurement of emitted fluorescence of a gas and for the measurement of transmitted light through a gas. The detector is close-coupled to an output end of a heated chromatographic column and eliminates the requirement of heated transfer tubes between the column and the detector.

5 Claims, 4 Drawing Figures

GAS CHROMATOGRAPH DETECTOR

BACKGROUND AND SUMMARY OF THE INVENTION

The present invention pertains to a gas chromatograph detector (GCD) for selective detection of compounds which have photo-responsive properties in their gas phase. More particularly the instant invention pertains to a detection chamber through which a compound in a gaseous-phase passes, wherein it is bombarded with light that causes the gas to fluoresce. Fluorescent properties of the gas are measured by light sensing devices adjacent to, and remote from, the detection chamber. The fluorescence producing light is generated at a site remote from the detection chamber.

Gas chromatography is used to separate organic compounds in a solution. A solution is vaporized and then passed through a chromatographic column, where the individual compounds are separated. One technique of identifying such separated compounds is through the use of a flame photometric detector (FPD), which ignites the subject gas after it has passed through a chromatographic column. The FPD destroys the compound in the analysis process. Ultraviolet or visible light absorption is also used to detect certain compounds.

A further method of detecting photo-responsive compounds is to dissolve gaseous effluents in a liquid solvent, and analyze the resultant solution fluorescence with traditional flow-through spectrofluorometric techniques.

Another method is the interface of a conventional spectrofluorometer to a gas chromatograph. The use of a spectrofluorometer, while providing information about compounds present, is an expensive technique which require the use of a machine which costs in excess of 20,000., and requires the use of heated transfer lines between the chromatograph and spectrofluorometer.

Rapid scanning instruments and flow-through cells, with heated transfer lines, have been used to effect low nanogram limits of detection of selected compounds. Silicon intensifier targets and laser excitation have also been used to detect low levels of aromatic hydrocarbons in their gas-phase.

For a variety of reasons, the above methods of detection are more suited to research laboratory practices than they are to real world use to detect the presence and quantity of photo-responsive compounds.

Of particular interest are groups of compounds with fluorescent photo responsive properties known as polynuclear aromatic compounds (PNA's). These compounds include many toxic chemicals as well as known carcinogens.

An object of the instant invention is to provide a detector which will detect sub-nanogram amounts of compounds which have photo-responsive properties in their gas-phase.

A further object of the instant invention is to provide a detector which will not require the use of heated transfer lines between a gas chromatograph and detector chamber.

A further object of the instant invention is to provide a gas chromatographic detector which will measure the fluorescent emission of compound in its gas phase through excitation by a light source.

Yet another object of the instant invention is to provide a detector which will measure light absorbance by a compound in its gas phase.

A preferred embodiment of the instant invention includes a gas chromatographic column, which is enclosed in a variable temperature oven, and further includes a vaporization block connected to an input end of the chromatographic column. A detector block is close-coupled to the output end of the chromatographic column by a light-tight coupling. The detector block includes a detection chamber which is connected to a fluorescence-producing light source by means of a special fiber-optic bundle, enclosed in a light-tight flexible conduit.

The detection chamber may be monitored by one or two light sensors, more particularly photo multiplier tubes (PMT). One PMT may be used to detect emitted fluorescence of a compound in its gas phase and the other PMT used to detect the amount of fluorescence producing light transmitted by a compound in its gas phase.

The detector block includes a heater element and a temperature sensing element which maintain the temperature of the block at a temperature substantially similar to that of the chromatographic column at the time the first effluents pass from the output end of the chromatographic column into the detector block.

The use of special fiber-optics to transmit flourescence producing light to the detection chamber and to transmit light from the detection chamber to an intensity detector enables the close coupling of the detector block to the chromatographic column and eliminates the need for heated transfer lines between the column and the detection chamber. The flexible light conduit is also a vibration dampener and enables a precise directing of light from the light source into the detector block without the light source being a physical part of the detector block.

These and other advantages and objects of the present invention will become more fully apparent as the description which fillows is read in conjunction with the accompanying drawings.

DETAILED DESCRIPTION OF THE PREFFERED EMBODIMENT

Figure 1:
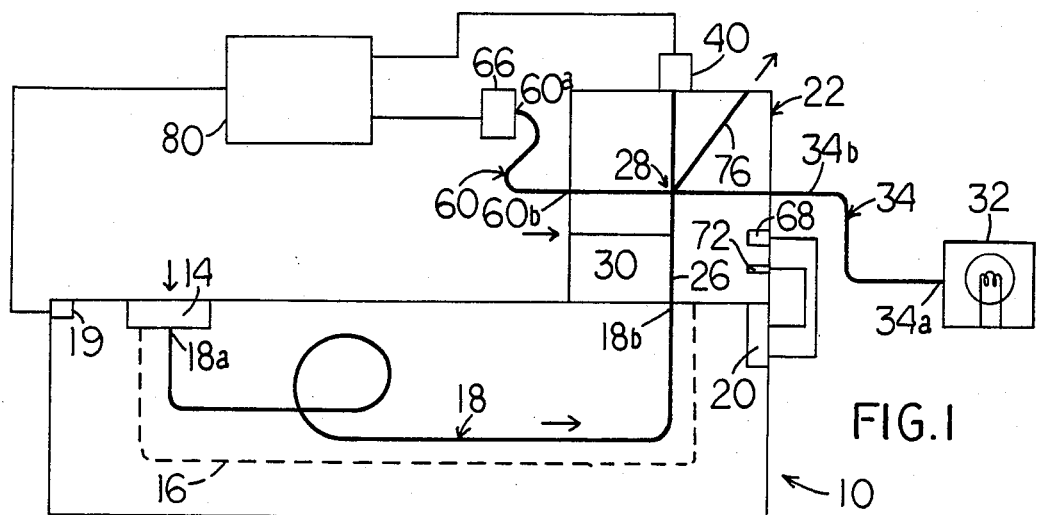
FIG. 1 is a schematic diagram showing a detector as contemplated herein, which includes a heated gas chromatographic and a fluorescence-detecting system.

Turning now to FIG. 1, a gas chromatographic detector (GCD) that detects selected compounds with photo-responsive properties is shown generally at 10. The detector includes a commercially available gas chromatograph 12 (Tracor Instruments model #565, in the preferred embodiment). Chromatograph 12 includes a vaporizor block 14, an oven or enclosure means 16, and a chromatographic column 18, with an input end 18a and an output end 18b. Chromatograph 12 also includes a timing mechanism 19 and a detector temperature control mechanism 20. Column 18 in the preferred embodiment is a two meter—two millimeter inside diameter glass tube packed with OV-1 packing material.

Figure 2:
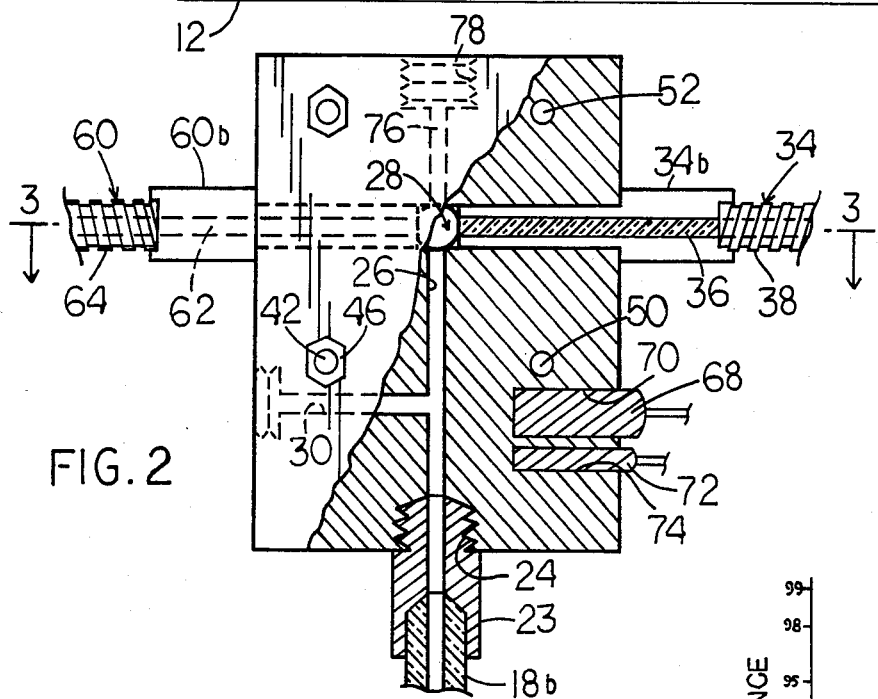
FIG. 2 is a front elevation of a detection block with portions broken away.
Figure 3:
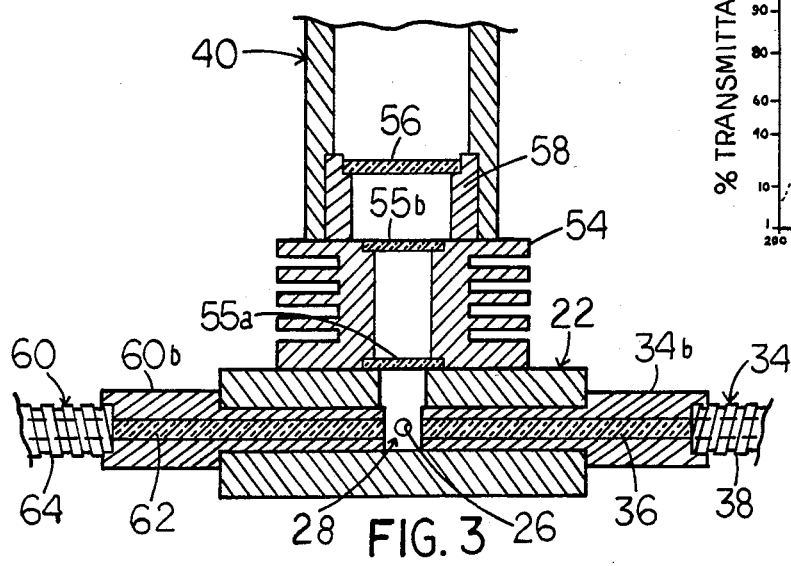
FIG. 3 is a top sectional view of a detection block taken generally along the line 3—3 in FIG. 2.

Immediately adjacent column output end 18b, and exterior of oven 16, is a detector block 22. Referring now to FIGS. 1-3 inclusive, detector block 22, which is formed of machined aluminum in the preferred embodiment, includes a threaded reception port 24, which attaches directly to column output end 18b, by means of a light tight connector 23. Port 24 connects with passage 26, which leads to an internal detection chamber 28. A make-up gas passage 30 connects with passage 26 between port 24 and chamber 28. All connections to block 22 are light tight.

Chamber 28 is connected to a light source 32 which generates light of a specified wavelength, to be discussed later. The light source in the preferred embodiment is a deuterium excitation-beam-source in a Tracor Model 970 HPLC (High-Pressure Liquid Chromatograph) detector. The source is located remote from the detection chamber and is air insulated from oven 16.

Light source 32, disposed in a spaced-air-insulated relation from enclosure means 16, is connected to detection chamber 28 by a first flexible light-transmitting conduit means 34. Conduit 34 has a light gathering end 34a which is connected to the deuterium excitation-beam-source. A stainless steel jack 34b is located on the other end of the light transmitting conduit, and is slip-fitted into detector block 22. Jack, or conduit chamber end, 34b slightly protrudes into detection chamber 28. a three millimeter diameter non-fluorescent quartz fiber-optic bundle 36 extends the length of conduit 34. A stainless steel flexible sheath 38 encloses bundle 36 along its length between conduit ends 34a and 34b.

Conduit 34, in its entirety, is heat resistant and heat insulating, and isolates chamber 28 from any vibration which may be produced by light source 32. Quartz bundle 36 is capable of transmitting ultraviolet light and is capable of withstanding extremely high temperatures. A fiber-optic bundle made of fused silicon exhibits similar qualities. Bundle 36 is bonded to jack 34 with high temperature epoxy.

The GCD of the instant invention is designed to measure two photo-responsive properties of a compound in a gas phase: fluorescence and absorption. To this end, two light measuring devices, or sensors are connected to detection chamber 28.

The first sensor detects the intensity of fluorescent light produced by a gas when excited by an appropriate light source. In the preferred embodiment, this unit takes the form of a photomultiplier tube (PMT) 40.

PMT 40 is secured to block 22 by four threaded shafts, as exemplified by shafts 42, 44, which pass through block 22 and are secured by nuts 46, 48, respectively. Shafts 42, 44 pass through bores in block 22, as exemplified by bores 50, 52, as shown in the cut-away portion of FIG. 2. A heat sink 54 provides heat insulation for PMT 40 from block 22. Two pyrex PMT windows, 55a and 55b, are mounted in heat sink 54 to further insulate PMT 40 from the heat of block 22 and the hot gas traversing chamber 28. A filter 56 is mounted in a filter holder 58 between detection chamber 28 and a sensing portion (not shown) of PMT 40. Filter 56 may be of the cut-on or band-pass type.

The second photo-responsive property which is measured is absorption. A second flexible light-transmitting conduit means 60 is mounted in block 22. Conduit 60 includes a stainless steel, slip-fitted jack, or conduit chamber end 60b, a fiber-optic bundle 62 and a stainless steel sheath 64. Conduit 60 slightly protrudes into chamber 28, opposite and coaxial with first conduit chamber end 34b, and terminates with a remote end 60a in an absorption measuring PMT 66. PMT 66 includes a filter (not shown) of the cut-on or band-pass type between the second conduit and the sensor portion of PMT 66.

Block 22 includes a heating unit 68 which is received in a heater receptacle 70, and a temperature sensor 72 which is received in a temperature sensor receptacle 74. Heater 68 and sensor 72 are connected to temperature control mechanism 20, of chromatograph 12, which adjusts the temperature of block 22, according to a predetermined temperature profile.

A discharge passage 76 connects chamber 28 with discharge port 78. Gas passes out of block 22 through port 78, which is light tight, and then to suitable disposal or capture facilities. The detector of the instant invention is non-destructive, so long as the subject compound is not photo-chemically instable.

Chromatograph 12 provides temperature control for column 18 over a selected temperature range. Timer mechanism 19 measures elapsed time from the entry of compound in its gas phase at column input end 18a to a second time when a particular compound arrives at detection chamber 28. Timing data from 19 and intensity data from PMT's 40, 66, is input into an integrator 80, a Hewlett-Packard 3390A integrator in the preferred embodiment.

Limits of detection and system sensitivity for a group of selected aromatic compounds are set forth in Table I below:

TABLE I

| | GAS-PHASE FLUORESCENCE GC DETECTION OF SELECTED AROMATIC COMPOUNDS | | | | | |
|---|---|---|---|---|---|---|
| Compound (purity) | Stock Solution $\mu g/\mu l$ | Absorbance Max. $\lambda$ In nm $\pm$ 5 nm | Detection[1] Limit (ng) | Detection[2] Limit (ng) | Linear[3] Range (ng) | Sensitivity[3] $(ng^{-1})$ |
| Naphthalene (98) | .23 | 260 | 8.8 | 17 | 42–2300 | 0.02 |
| acenaphthene (99) | .12 | 220 | 0.6 | 9 | 9–1200 | 0.13 |
| 2,3,5-trimethylnaphthalene | | | 17 | | | |
| fluorene (98) | .15 | 255 | 1.5 | 5 | 7–1500 | 0.11 |
| phenanthrene (98) | | 240 | 4 | | | |
| anthracene (99.9) | .12 | 245 | 0.4 | 10 | 2–1200 | 2.2 |
| 2-methylanthracene (97) | .08 | 240 | 0.3 | 4 | 1–800 | 0.35 |
| 2-3thylanthracene (98) | | | 3 | | | |
| fluoranthene (98) | .04 | 270 | 4.5 | 2 | 8–400 | 0.29 |
| 9,10-dimethylanthracene (99) | | | 1 | | | |
| pyrene (99) | .04 | 260 | 2.3 | 1 | 3–400 | 1.8 |
| 2,3-benzofluorene | | | 0.4 | | | |
| 9-phenylanthracene (98) | | | 4 | | | |
| 1,2-benzanthracene (99) | | | 0.6 | | | |
| triphenylene (98) | | 250 | | 4 | | |
| 2,3-benzanthracene | | | 1 | | | |

TABLE I-continued
GAS-PHASE FLUORESCENCE GC DETECTION OF SELECTED AROMATIC COMPOUNDS

| | | | | | | |
|---|---|---|---|---|---|---|
| chrysene (95) | .02 | 250 | 0.6 | 0.8 | 2–200 | 1.1 |
| 7,12-dimethylbenzanthracene (97) | .04 | 270 | 8.3 | 1 | | |
| perylene (97) | .02 | 240 | 0.6 | 2 | 3–200 | 0.5 |
| 1,2,5,6-dibenzanthracene (97) | | | 1 | | | |
| 1,2,3,4-dibenzanthracene (97) | .02 | 260 | 0.9 | 0.4 | 4–200 | 0.25 |

| λ Of Excitation Light | Filter 56 | Oven Temperature Profile | Make-Up Gas |
|---|---|---|---|
| [1]Absorbance Max | Band-Pass F1 | 150° C. to 260°C. @ 15° C./min | 35mL N$_2$/min |
| [2]250 nm | Cut-on F2(340 nm) | ISOTHERMAL 230° C. | 35mL N$_2$/min |
| [3]260 nm | Band-Pass F1 | 150° C. to 260° C. @ 15° C./min | 35mL Hc/min |

SYSTEM CALIBRATION

Turning now to Table I, a group of selected aromatic compounds are listed. A solution of 1:1 hexane:methylene chloride is used to dilute aromatic hydrocarbons, of the purity indicated in Table I. The solution with the known aromatic hydrocarbon is injected into vaporizer block 14, which is maintained at approximately 300° C., a temperature which is sufficient to gasify an aromatic hydrocarbon. Chromatograph 12 is generally programmed for a ramp-type temperature increase from approximately 150° C. to 260° C., at a rate of 15° C. per minute. Transit time of the gas through chromatographic column 18 is measured by timer mechanism 19. Transit time of a gas through the column is indicative of compound identity.

Once the gas reaches the detector block, it is bombarded with light from source 32 substantially in the ultraviolet range, which causes the gas to fluoresce. Fluorescent intensity is measured by PMT 40. PMT 40 produces an electrical signal which is proportional to the level of fluorescent intensity. Similarly, the amount of light transmitted through the gas is indicative of the absorbance characteristics of the gas, and the intensity of transmitted light is measured by PMT 66. The intensity of fluorescence or transmisivity is indicative of the amount of a specific compound present in a sample.

Figure 4:
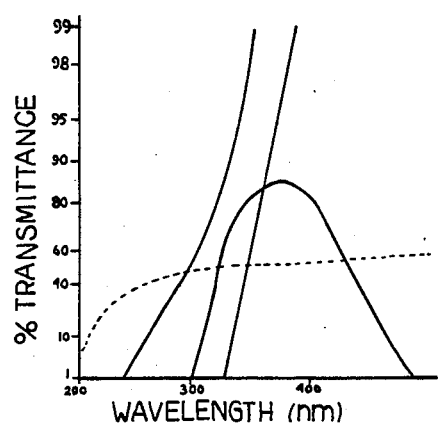
FIG. 4 is a graphic representation of transmittance vs. wavelength relations of the optical components of the (GCD).

Filter 56 may be of the type which passes light greater than a certain wavelength (Cut-On Type F1) or one which passes all light within a certain wavelength range (Band-Pass F2). A Cut-On type filter has been experimentally found to be effective if it passes light of a wavelength greater than 340 nm. A band-pass filter (F2) may also be used when looking for a single specific compound of known fluorescence wavelength. The optical transmission characteristics of the two filter types, (F1), (F2) the PMT windows (PMT) and the fiber optic bundles (FO), as used in the preferred embodiment, are shown in FIG. 4. A band pass filter transparents to other wavelengths may be used when using the apparatus for detection of a specific compound.

Once data has been gathered for individual aromatic compounds, a stock solution containing certain compounds, as indicated by the amounts in Table I, was made up and introduced into the system. The stock solution was diluted with reagent grade solvents to determine specroscopic parameters, sensitivities, and limits of detection. Further experimentation with technical grade solvents were made to determine the sensitivity of the system to interference by non-aromatic compounds.

A flow rate of gas through detection chamber 28 at a rate less than 30-milliliters/minute was found to decrease sensitivity. The injection of nitrogen, helium, or argon, as a make-up gas, through make-up gas passage 30 increased total flow to 40-milliliters per minute or greater, thereby maintaining detector sensitivity.

The detector as described is sufficiently sensitive to detect subnanogram levels of compounds which fluoresce in their gas-phase. The device is particularly suited to detect subnanogram levels of polynuclear aromatic hydrocarbons (PNA's) and is not subject to interference from non-fluorescing compounds. Additionally, the detector as described does not require extensive sample clean-up procedures presently required in existing detectors when sampling for PNA's in complex sample matricies.

SYSTEM OPERATION

A sample of material which is believed to contain a photo-responsive compound, generally, a PNA, is injected into vaporizer block 14. The temperature within block 14 is maintained at approximately 300° C., a temperature which is sufficient to gasify PNA's contained within the injected solution. Once the solution is gasified, the compound in its gas phase transmits the chromatographic column. Transit time of the gas phase PNA through the column is on the order of 15 minutes.

Chromatographic oven 16 is generally programmed for a ramp-type increase in temperature, to provide a more efficient separation of compounds within the column, although isothermal columnation has also proved useful in some instances.

Once the gas reaches the detector block, which is heated to approximately 250° C., the gas is bombarded with light substantially in the ultraviolet range. The gas fluoresces, the level of fluorescense is detected by PMT 40. Light transmitted through the gas is detected by PMT 66. Non-absorptive compounds are completely ignored by the detectors, and non-fluorescent compounds are ignored by PMT 40. Maximum sensitivity is obtained by inserting conduit chamber ends 34b and 60b into chamber 28 a distance of 1 mm.

The transit time of the compound from vaporization to detection provides qualitative data regarding compound identity. Transit time of a sample is compared with those of known PNA compounds to determine the presence and identity of PNA's in an unknown compound.

The level of photo-response measured by the PMT's is indicative of compound quantity. PMT output, as recorded by integrator 80, appear as peaks and valleys on a strip chart. The area under the peaks is integrated to provide quantitative data.

As previously noted, the use of the fiber optic cables thermally isolates the light source from the heated detector block, and isolates the detector block from vibrations which are produced by monochromatic light sources. Heat produced by the chromatographic enclosure can adversely effect the wavelength or intensity of light produced by a monochromatic light source. Vibration caused by the light source can affect the sensitivity of the detector chamber.

Thus, an apparatus and a method of gas-phase detection of fluorescent compounds has been disclosed.

These compounds include toxins and known carcinogens. Additionally, since petroleum resources contain PNA's, oil spills may be traced surface or sub-surface by monitoring PNA's. Further, the source of an oil spill may be determined by analysis of a spill sample for PNA's known to be peculiar to a geographic-specific oil source.

While a preferred embodiment of the invention has been described, it is appreciated that variations and modifications made may be made without departing from the spirit of the invention.

It is claimed and desired to secure by Letters Patent:

1. A gas chromatographic detector for selective detection of compounds which have photo-responsive properties in a gas-phase, which comprises
   a chromatographic column with input and output ends, through which compounds travel while in a gas phase, and an oven encompassing said column useable in establishing a selected temperature above ambient temperature within said column,
   a detection block disposed directly adjacent and externally of said oven having an internal detection chamber, said block being directly connected to the output end of said column,
   a light source disposed in spaced-air-insulated relation from the oven, and
   first flexible light-transmitting conduit means connecting said light source with said detection chamber in said block.

2. The detector of claim 1, which further includes a second flexible light-transmitting conduit means and light-measuring means, one end of said second conduit means is connected to said detection chamber, and the opposite end of the second conduit means is connected to said light measuring means, said light-measuring means detecting a photo-response within said chamber of a compound in a gas-phase.

3. The detector of claim 2, wherein said first and second flexible light-transmitting conduit means comprises a shielded, fiber-optic bundle.

4. The detector of claim 3, wherein said bundle is made of material selected from the group consisting of quartz, and fused silicon.

5. The detector of claim 2, wherein each of said first and second flexible light-transmitting conduit means comprises a shielded fiber optic bundle terminating in a jack with the bundle exposed at a remote end of the jack, and the jack detachably mounted on said block.

* * * * *